United States Patent [19]

Fischell et al.

[11] Patent Number: 5,795,286
[45] Date of Patent: Aug. 18, 1998

[54] RADIOISOTOPE IMPREGNATED SHEET OF BIOCOMPATIBLE MATERIAL FOR PREVENTING SCAR TISSUE FORMATION

[75] Inventors: Robert E. Fischell, Dayton, Md.; David R. Fischell, Fair Haven, N.J.

[73] Assignee: Cathco, Inc., Dayton, Md.

[21] Appl. No.: 698,577

[22] Filed: Aug. 15, 1996

[51] Int. Cl.⁶ ................................................. A61N 5/00
[52] U.S. Cl. ................................................. 600/3
[58] Field of Search ................................... 600/1–8

[56] References Cited

U.S. PATENT DOCUMENTS 5,059,166  10/1991  Fischell ........................... 600/3

FOREIGN PATENT DOCUMENTS 0292630  11/1988  European Pat. Off. ............ 600/1

Primary Examiner—John P. Lacyk

[57] ABSTRACT

This invention is a radioisotope impregnated material sheet or mesh designed to be placed between internal body tissues to prevent the formation of post-operative adhesions, which adhesions are really scar tissue formation. This mesh or gauze into which the isotope is placed may be either a permanent implant or it may be biodegradable. By impregnating an existing product such as the Johnson & Johnson SURGICEL™ absorbable hemostat gauze-like sheet with a beta emitting radioisotope such as phosphorous-32 with has a relatively short effective range of approximately 4 mm, the biodegradable mesh would act as a barrier to cell proliferation and hence be a deterrent to the formation of adhesions.

13 Claims, 2 Drawing Sheets

RADIOISOTOPE IMPREGNATED SHEET OF BIOCOMPATIBLE MATERIAL FOR PREVENTING SCAR TISSUE FORMATION

FIELD OF USE

This invention is in the field of materials used to prevent post-operative scar tissue proliferation which can result in surgical adhesions.

BACKGROUND OF THE INVENTION

Post-operative adhesions are a major problem following abdominal and other surgical procedures. These adhesions are caused by the unwanted proliferation of scar tissue between internal tissues and structures of the human body. Several companies have developed sheets of biodegradable mesh which can be placed between these structures to reduce the tissue growth. None are entirely effective as the cells typically grow through the mesh. U.S. Pat. No. 5,059,166 (which is included herein by reference) describes the use of a beta emitting radioisotope to reduce the proliferation of tissue through the wires of a wire mesh tube (a stent) placed into an artery.

SUMMARY OF THE INVENTION

This invention is a radioisotope impregnated material sheet or mesh designed to be placed between internal body tissues to prevent the formation of post-operative adhesions, which adhesions are really scar tissue formation. This mesh or gauze into which the isotope is placed may be either a permanent implant or it may be biodegradable. By impregnating an existing product such as the Johnson & Johnson SURGICEL™ absorbable hemostat gauze-like sheet with a beta emitting radioisotope such as phosphorous-32 with has a relatively short effective range of approximately 4 mm, the biodegradable mesh would act as a barrier to cell proliferation and hence be a deterrent to the formation of adhesions.

Thus it is an object of this invention to have a sheet of material that can be placed between internal body tissues, the material being impregnated or coated with a radioisotope to reduce the scar tissue proliferation between adjacent layers of the human tissue.

Another object of this invention is to have a biodegradable radioisotope sheet of material or mesh.

Still another object of this invention is to have the radioisotope be a pure beta emitter.

Another object of this invention is to have the beta emitter be phosphorous-32.

Still another object is to have the activity of phosphorous-32 on the sheet of material or mesh be between 0.2 and 2 µCi per square centimeter.

Yet another object is to have the activity of phosphorous-32 be between 2 and 20 µCi per square centimeter.

These and other objects and advantages of this invention will become obvious to a person of ordinary skill in this art upon reading of the detailed description of this invention including associated drawings.

DETAILED DESCRIPTION OF THE DRAWINGS

Figure 1:
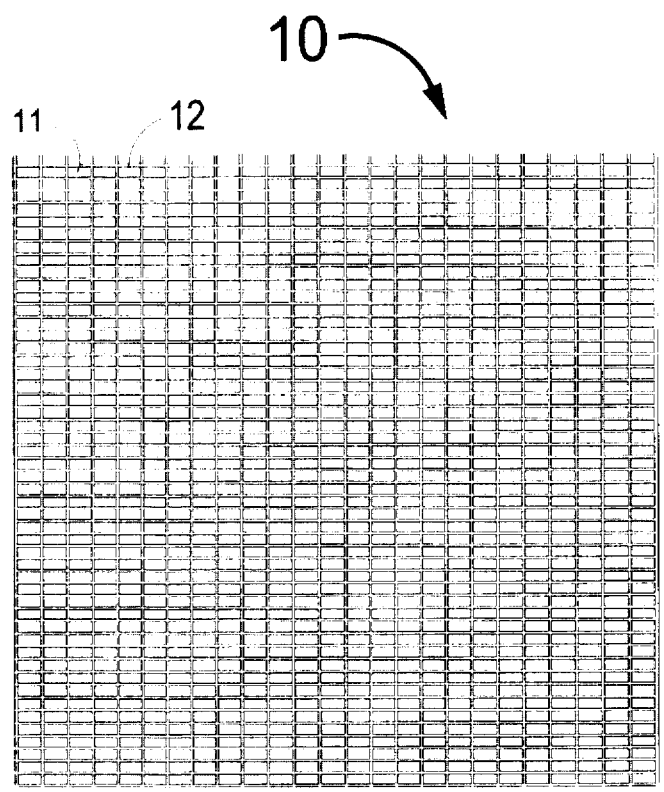
FIG. 1 is a plan view of a sheet of radioisotope impregnated mesh.

FIG. 1 shows an absorbable hemostat mesh sheet 10 with mesh strands 12 and open spaces 11. The sheet 10 is designed to be placed post-operatively between internal body tissues. The mesh strands 12 can be made from oxidized regenerated cellulose or other biodegradable materials with the radioisotope either embedded within the strands or coated onto the outer surfaces of the strands.

Figure 2:
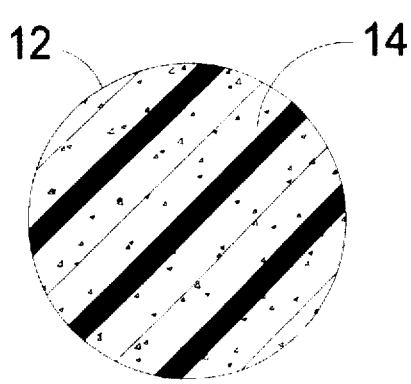
FIG. 2 is an enlargement of the cross section of a single strand of the mesh where the radioisotope is embedded within the strand.

FIG. 2 is an enlargement of a cross section of a single strand 12 of the mesh 10 in which the radioisotope 14 is embedded within the strand 12.

Figure 3:
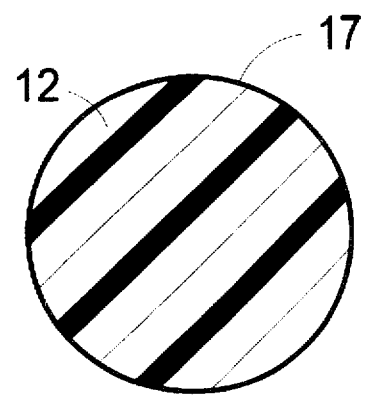
FIG. 3 is an enlargement of the cross section of a single strand of the mesh where the radioisotope is coated onto the strand.

FIG. 3 is an enlargement of the cross section of a single strand 16 of the mesh where the radioisotope 17 is coated onto the exterior surface of the strand.

Figure 4:
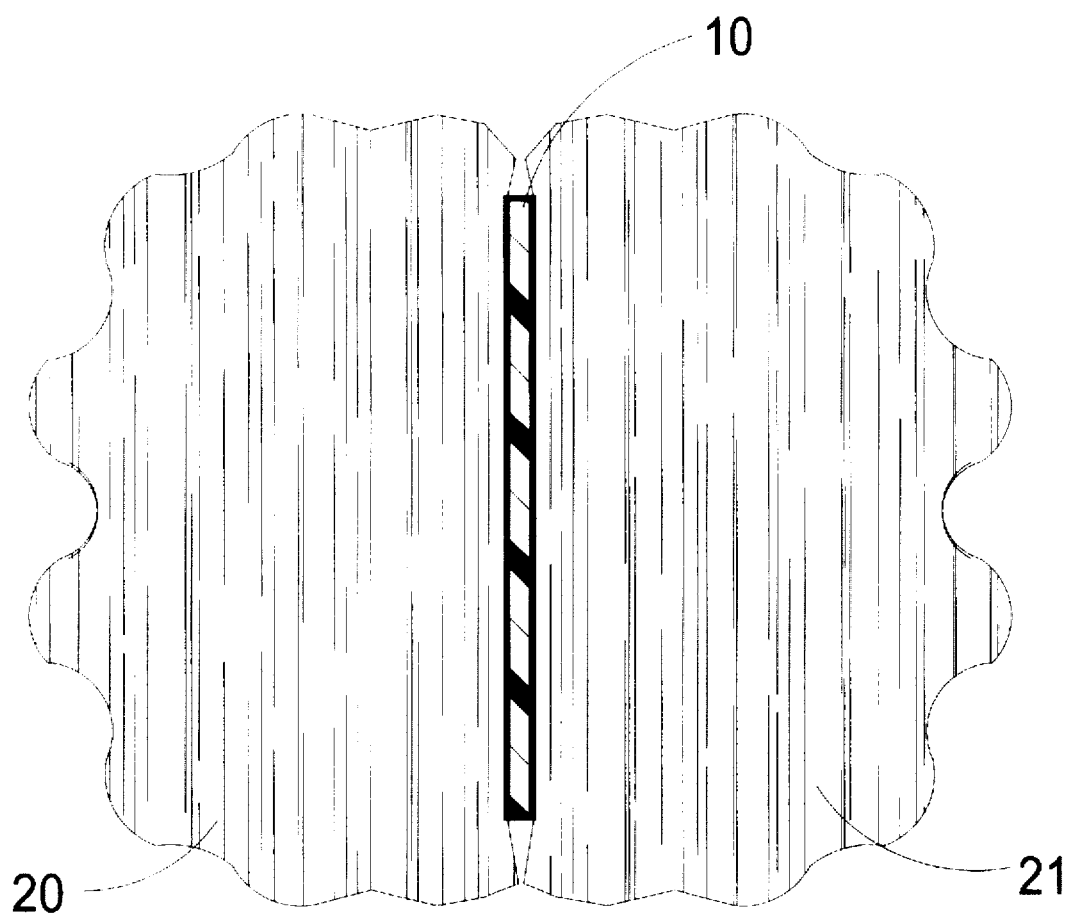
FIG. 4 shows a cross section of the radioisotope impregnated or coated mesh placed between two layers of tissue of the human body.

FIG. 4 shows the radioisotope impregnated mesh 10 placed between two adjacent tissues 20 and 21 of a human body. The mesh 10 would be inserted during a surgical procedure typically just before closing of the surgical incision. When the biodegradable mesh 10 dissolves or is absorbed into the tissue 20 or 21, because the radioisotope is not encapsulated within a non-soluble structure, the radioisotope embedded into or coated onto the mesh 10 will become dispersed into the tissue 20 or 21.

The radioisotopes that may be used are primarily beta emitters such as phosphorous-32, phosphorous-33, or calcium 45. If phosphorus-32 is used, the activity range should be between 0.2 and 20 $\mu Ci/cm^2$. If the mesh is coated, an insoluble suspension of P-32 such as that used to treat ovarian cancer would be appropriate either by itself or mixed with another biodegradable material.

Although a mesh has been discussed herein, more generally, a radioisotope can be made to be part of any sheet of material that is or is not biodegradable, as long as the sheet of material is biocompatible. In any case the radiation from the radioisotope that is included within at least part of the sheet of material will decrease cellular proliferation and therefore decrease the formation of scar tissue and adhesions.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A biodegradable sheet of material adapted for implantation between tissues of a human body, at least part of said sheet of material including a radioisotope, said radioisotope being placed within a soluble structure which is said biodegradable sheet of material so that the radioisotope becomes dispersed into the human body.

2. The apparatus of claim 1 wherein the radioisotope is embedded within the sheet of material.

3. The apparatus of claim 1 wherein the radioisotope is coated onto the sheet of material.

4. The apparatus of claim 1 wherein the radioisotope is predominantly a beta emitter.

5. The apparatus of claim 4 wherein the beta emitter is phosphorous-32.

6. The apparatus of claim 1 wherein the sheet of material is in the form of a mesh.

7. The apparatus of claim 1 wherein the radioisotope is embedded within the biodegradable material.

8. The apparatus of claim 1 wherein the radioisotope is coated onto the biodegradable material.

9. The apparatus of claim 1 wherein the radioisotope is predominantly a beta emitter.

10. A method for the prevention of scar tissue formation and adhesions associated with a surgical procedure, the method comprising the following steps:

a) place a radioisotope that is free from encapsulation into a non-soluble structure into a biodegradable sheet of material; and b) place the sheet of material containing the radioisotope into a human body between tissues that are separated by a surgical incision.

11. The method of claim 10 including the step of closing the surgical incision after the sheet of material is placed between the separated tissues.

12. A biodegradable material adapted for implantation between tissues of a human body, at least part of said biodegradable material including a radioisotope, said biodegradable material and said radioisotope each being adapted to be absorbed into the human body.

13. The apparatus of claim 12 wherein the beta emitter is phosphorous-32.

* * * * *